US007094234B1

(12) United States Patent
Lennox

(10) Patent No.: US 7,094,234 B1
(45) Date of Patent: Aug. 22, 2006

(54) INTERSTITIAL BRAIN COOLING PROBE AND SHEATH APPARATUS

(75) Inventor: Charles D. Lennox, Hudson, NH (US)

(73) Assignee: MedCool, Inc., Westwood, MA (US)

( * ) Notice: Subject to any disclaimer, the term of this patent is extended or adjusted under 35 U.S.C. 154(b) by 261 days.

(21) Appl. No.: 10/229,218

(22) Filed: Aug. 27, 2002

Related U.S. Application Data

(60) Provisional application No. 60/315,097, filed on Aug. 27, 2001.

(51) Int. Cl.
*A61B 18/18* (2006.01)

(52) U.S. Cl. ............... 606/49; 607/104; 607/100; 607/115; 607/116; 606/22; 606/23; 606/40; 606/41

(58) Field of Classification Search ............ 606/41, 606/42, 45–52, 40, 20–24; 607/100–102, 607/104–106, 115, 116, 122
See application file for complete search history.

(56) References Cited

U.S. PATENT DOCUMENTS

| 3,298,371 | A | | 1/1967 | Lee ......................... 606/23 |
| 3,971,383 | A | | 7/1976 | van Gerven ............. 128/303.1 |
| 5,139,496 | A | | 8/1992 | Hed ......................... 606/23 |
| 5,423,807 | A | * | 6/1995 | Milder ........................ 606/20 |
| 5,433,717 | A | * | 7/1995 | Rubinsky et al. ............. 606/20 |
| 5,452,582 | A | * | 9/1995 | Longsworth ................ 62/51.2 |
| 5,577,387 | A | | 11/1996 | Maytal ....................... 62/51.2 |
| 5,620,479 | A | * | 4/1997 | Diederich ...................... 601/3 |
| 5,649,936 | A | | 7/1997 | Real ......................... 606/130 |
| 5,910,104 | A | | 6/1999 | Dobak, III et al. ......... 600/121 |
| 5,921,982 | A | * | 7/1999 | Lesh et al. ................... 606/41 |
| 6,248,126 | B1 | * | 6/2001 | Lesser et al. ............... 607/113 |
| 6,251,105 | B1 | | 6/2001 | Mikus et al. ................ 606/22 |
| 6,272,370 | B1 | * | 8/2001 | Gillies et al. .............. 600/411 |
| 6,379,348 | B1 | * | 4/2002 | Onik .......................... 606/21 |
| 6,428,531 | B1 | * | 8/2002 | Visuri et al. ................. 606/7 |
| 6,432,102 | B1 | * | 8/2002 | Joye et al. ................... 606/21 |
| 6,481,439 | B1 | * | 11/2002 | Lewis et al. ................ 128/898 |
| 6,669,687 | B1 | * | 12/2003 | Saadat ........................ 606/14 |

* cited by examiner

*Primary Examiner*—Rosiland Rollins
(74) *Attorney, Agent, or Firm*—Thomas J. Engellenner; Charlton Shen Nutter McClennen & Fish LLP

(57) ABSTRACT

Disclosed is an apparatus and method for preventing secondary ischemic injury in the brain. The apparatus includes an interstitial brain probe and an introducer sheath, which are placed into an ischemic region of the brain by stereotaxic surgical technique. The interstitial brain probe and introducer sheath provide for thermal coagulation to provide hemostasis, aspiration of blood clots, infusion of therapeutic agents, and localized hypothermia within an ischemic region of the brain. The interstitial brain probe cools an ischemic region of the brain from within the ischemic region, and cooling is substantially limited to the ischemic region. Cooling is provided for a period of time greater than one hour.

39 Claims, 15 Drawing Sheets

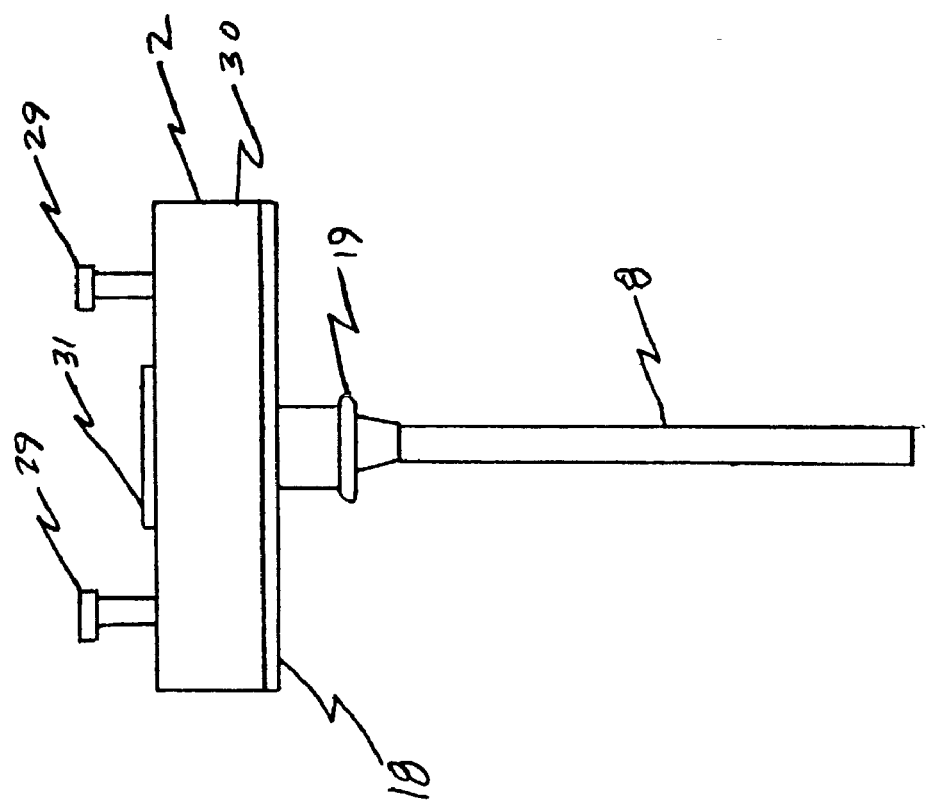

INTERSTITIAL BRAIN COOLING PROBE AND SHEATH APPARATUS

CROSS REFERENCE TO RELATED APPLICATIONS

This application is entitled to the benefit of Provisional Patent Application Ser. No. 60/315,097 filed 2001 Aug. 27.

BACKGROUND

1. Field of Invention

This invention relates to apparatus for inducing local cerebral hypothermia consisting of a stereotaxic interstitial brain cooling probe, introducer sheath, and related accessories.

2. Description of Prior Art

Stroke is a leading cause of death and disability. It is estimated that over 725,000 people suffer a major stroke in the United States each year, and that over 100,000 of these people die. There are two main categories of stroke: ischemic and hemorrhagic. A blockage in an artery in the brain causes ischemic stroke, and a rupture in an artery in the brain causes hemorrhagic stroke. There are approximately 600,000 ischemic stokes, and 125,000 hemorrhagic strokes in the United States each year.

Within the last decade there has been a marked increase in understanding why and how brain cells die from ischemic stroke. Cells within an infarction zone have dramatically reduced blood flow of 20% of normal or less. Cells within this infarction zone will be irreversibly damaged within a few minutes. Surrounding the infarcted zone is a volume of tissue called the "ischemic penumbra" or "transitional zone" in which blood flow is between 20% and 50% of normal. Cells in this area are endangered, but not irreversibly damaged. Ischemia in the infarction zone, and in the ischemic penumbra causes the ischemic cells to release excitatory proteins which migrate into surrounding tissues triggering a hyper metabolic response that leads to cell death beyond the infarction zone and the ischemic penumbra. This hyper metabolic response triggers inflammation, edema, local and global pyrexia, cerebral hypertension, apoptosis, and an increase in intra-cranial pressure causing a cascade of cell injury and death. Nowhere in the art is a mechanism described that can effectively prevent or limit the migration of excitatory proteins from ischemic tissue, to surrounding normal tissue in the brain, and simultaneously resolve the ischemic penumbra.

Hypothermia has long been known to be neuroprotective. There are countless anecdotes where resuscitation of cold water drowning victims has been successfully achieved after an extended period of cardiac arrest with few untoward effects. In the 1970's deep systemic hypothermia (core temperature below 30 Deg. C.) was evaluated as a therapy for stoke and other cerebral indications but was abandoned due severe systemic complications. Since 1990 there has been a significant effort to evaluate mild systemic hypothermia (core temperature of 32 to 34 Deg. C.) as a therapy for stroke in animal models, and more recently in clinical trials.

Mild systemic hypothermia has been shown to significantly reduce infarct size, and improve neurological outcome in animal models.

Recent clinical reports of have indicated that mild systemic hypothermia may have a significant positive benefit for patients suffering severe focal ischemic stroke.

Swartz et. al. recently reported treating 25 patients with severe MCA territory stroke with systemic hypothermia at 33 deg. C. for 48 to 72 hours. 56% of the patients survived; historical controls indicated that a survival rate of less than 20% would normally be expected. This study also demonstrated that mild hypothermia is effective in reducing critical rises in intra-cranial pressure.

At the 26th Annual International Stroke Conference held this past January, Krieger et al reported treating 10 patients with 19 matched controls with systemic hypothermia at 32 Deg. C. for 48 hours. At 3 months 50% of the patients in the treatment arm had a "good" neurological outcome vs. 10% in the control arm. The initiation of a 350 patient randomized study was announced.

There is a large body of evidence in the scientific literature, mostly developed within the past ten years, which demonstrates that hypothermia has a broad spectrum of neuroprotective effects against ischemia.

Hypothermia:
  Reduces metabolic rate
  Lowers ATP requirements
  Reduces lactic acidosis
  Reduces production of excitatory proteins
  Reduces edema
  Reduces neutrophil accumulation
  Reduces glial cell activation
  Stabilizes the blood/brain barrier Hypothermia's effect on metabolic rate and production of excitatory proteins is temperature dependent, where the lower the temperature, the greater the neuroprotective effect. Hypothermia's effect on edema stabilizes at about 33 Deg. C. with no further benefit at lower temperatures.

Early clinical experience has demonstrated that sustained systemic hypothermia below 30 Deg. C. is impractical. Complications of systemic hypothermia below 30 Deg. C. include cardiac arrhythmia and arrest, hemorrhage due to systemic coagulation disorders, pancreatitis, pneumonia, and death.

Recent clinical experience has demonstrated that sustained systemic hypothermia at 32 to 33 Deg. C. may be practical. The most common reported systemic complication is pneumonia. However, for a patient to tolerate even mild systemic hypothermia, full anesthesia is required for the duration of the therapy. Also, rewarming following hypothermia is considered a critical phase of the therapy. An uncontrollable rise in intra-cranial pressure has been a frequent event during the rewarming phase. The risks of sustained mild hypothermia beyond 72 hours are unknown.

It has long been known that hypothermia causes vasoconstriction in the limbs, and vasodilation in vital organs. This is a basic mammalian survival mechanism where blood is directed to vital organs at the expense of the rest of the body during hypothermic challenge. The brain, and the heart, being the most vital organs, have the greatest capacity for vasodilation during hypothermic challenge.

It has been well documented that even mild systemic hypothermia reduces cerebral blood flow rate. In an animal model, cerebral blood flow rate decreases approximately 5% for each degree centigrade reduction in core temperature.

Kuluz et al demonstrated in a well-understood animal model that selective brain cooling, where the brain is cooled, and the body is maintained at normal temperature results in a significant increase in cortical cerebral blood flow rate. There was a 215% increase in cortical cerebral blood flow when the brain was cooled to 33 Deg. C., with a slight increase in cortical cerebral blood flow when the temperature was further lowered to 30 Deg. C. Cortical cerebral blood flow returned to base line when normal temperature was restored.

Kuluz suggests that hypothermia causes vasodilation, which is maximal at a temperature between 30 and 33 Deg. C. Although both systemic hypothermia and selective cerebral hypothermia both result in vasodilation, the suppressive effect of systemic hypothermia on cardiac output results in a net decrease in cerebral blood flow. When hypothermia is applied selectively to the brain, vasodilation of the blood vessels within the brain results in a decrease in cerebral vascular resistance relative to the rest of the body, resulting in an increase in cerebral blood flow. Kuluz also suggests that the neuroprotective effects of hypothermia may be more related to vasodilation than to biochemical mechanisms.

Intra-parenchymal brain temperature may exceed core body temperature by as much as 2.4 Deg. C. during the acute phase of focal ischemic stroke. Elevated brain temperature during the acute phase of a stroke is presumed to be the result of hyper-metabolic processes caused by ischemia. Although temperature within an infarction or the ischemic penumbra has not been measured during acute ischemic stroke, it is presumed to be at a higher temperature than the average brain temperature, which has been measured. This is based on the premise that excitatory proteins released by the ischemic brain tissue within the infarction and ischemic penumbra causes the rate of metabolic activity within the infarction and the ischemic penumbra to be greater than of the rest of the brain. The hyper-metabolic rate within the infarction and the ischemic penumbra, in combination with diminished blood flow results in a temperature within the infarction and ischemic penumbra, which exceeds the temperature in the rest of the brain.

During systemic hypothermia treatment of focal ischemic stroke, the temperature within the infarction and ischemic penumbra remain at a higher temperature than the rest of the brain and body. During local cerebral hypothermia, by design, the infarction and the ischemic penumbra are at lower temperatures than the rest of the brain.

Since systemic hypothermia is limited by patient tolerance to 32 to 33 Deg. C., and the infarction and ischemic penumbra remain at higher temperatures than surrounding brain tissue, maximal vasodilation effect is not likely to be achieved. Also, the suppressive effect of systemic hypothermia on the release of excitatory proteins from within the infarction and the inner core of the ischemic penumbra are likely to be minimal or non-existent.

Local cerebral hypothermia provides a temperature profile within the affected area of the brain that provides maximum vasodilation within the ischemic penumbra without reducing cardiac output, and provides for significant suppression of excitatory protein release from within the infarction.

There are several examples in the art where catheters are constructed with a cooling means, which is placed into the carotid artery to cool the blood entering the head. This offers an advantage over systemic hypothermia, since it provides a means to cool the head to lower temperatures than the rest of the body, but it still results in systemic hypothermia. Also, since the scientific evidence suggests that hypothermia must be maintained for extended periods of time, there is a great risk that clots will form on the catheters and migrate into the brain leading to further episodes of stroke. The mechanism of cooling a zone of infarction in the brain, or the surrounding transitional zone with this approach is the same as with systemic hypothermia, and does not overcome the significant limitations as described above.

Often, an infarction will hemorrhage spontaneously and lead to a poor outcome for the patient. Spontaneous hemorrhage in an infarction is believed to be caused by a combination of the deterioration of the blood vessels, and a local increase in blood pressure due to ischemia. There is a wide spread perception held by neurosurgeons that if a probe is placed into an infarction in the brain there is a significant risk that the trauma of placing the probe will cause hemorrhage due to the frail nature of the blood vessels in the infarction.

There are numerous examples of interstitial cooling probes in the art. Nowhere in the art is it suggested that interstitial cooling probes may be used to treat stroke, and nowhere in the art is there an example of a cooling probe that may be practically fixated to the head and left indwelling in the brain for the extended periods of time required for effective hypothermia treatment of stroke, that also provides for a means to coagulate the core of an ischemic lesion sufficiently to mitigate the risk of hemorrhage.

SUMMARY

Therefore, it is an object of this invention to provide apparatus for treating stroke. Another object of this invention is to provide apparatus for treating focal ischemic stroke. Another object of this invention is to provide apparatus for inducing local hypothermia in the brain.

In accordance with one aspect of this invention, apparatus for treating stroke includes an interstitial probe constructed for placement into the brain by stereotaxic radiological guidance, where the distal tip of the probe includes a heating mechanism with sufficient heating capacity to coagulate a volume of infarcted tissue surrounding the distal tip sufficiently to mitigate the risk of hemorrhage, and where the distal tip of the probe includes a cooling mechanism with sufficient heat absorbing capability to cool a volume of brain tissue to the degree, and for a period of time sufficient to mitigate the effects of stroke. In another aspect of this invention, apparatus for treating stroke is an interstitial probe where the distal end of the probe contains a mechanism for heating tissue surrounding the distal tip of the probe, and a mechanism for cooling tissue surrounding the distal tip of the probe, and a mechanism near the distal tip to sense an effect of said heating and said cooling. In accordance with another aspect of this invention, apparatus for treating stroke consists of an interstitial brain probe, and an introducer sheath, where the interstitial brain probe and the introducer sheath are constructed to integrally provide for a mechanism for fixating said apparatus to the head. In accordance with another aspect of this invention, apparatus for treating stroke consists of an interstitial brain probe, and an introducer sheath, where the interstitial brain probe and the introducer sheath are constructed to integrally provide for a mechanism for accommodating temporal changes in brain morphology. In accordance with another aspect of this invention, apparatus for treating stroke consists of an interstitial brain probe, and an introducer sheath, where the interstitial brain probe and the introducer sheath are constructed to integrally provide for sealing the craniotomy to prevent infection. In accordance with another aspect of this invention, apparatus for treating stroke consists of an interstitial brain probe, and an introducer sheath, where the interstitial brain probe and the introducer sheath are constructed to integrally provide for a mechanism for providing aspiration of blood in case of hemorrhage. In accordance with another aspect of this invention, apparatus for treating stroke consists of an interstitial brain probe, and an introducer sheath, where the interstitial brain probe and the introducer sheath are constructed to integrally provide for a mechanism for interstitial delivery of a therapeutic substance into the brain. In accordance with another aspect of this invention, apparatus for treating stroke is a surgical kit consisting of an interstitial brain probe, an introducer sheath, a stereotaxic access needle and a protective shield.

Objects and Advantages

Accordingly, besides the objects and advantages of the apparatus to treat stroke described in my patent above, several objects and advantages of the present invention are:
  (a) to provide apparatus for coagulating a portion of a volume of brain tissue at risk from stroke, and for inducing localized hypothermia to a volume of brain tissue at risk from stroke according to the objectives stated above;
  (b) to provide an interstitial brain probe apparatus that is constructed to be placed by stereotaxic radiological guidance by well known surgical methods;
  (c) to provide an interstitial brain probe apparatus that is constructed to provide for long term indwelling;
  (d) to provide an interstitial brain probe apparatus that is constructed to provide for protection against infection;
  (e) to provide an interstitial brain probe apparatus that is constructed to provide for a means to sense a response to heating and cooling;
  (f) to provide an interstitial brain probe apparatus that is constructed to provide for a means to control the degree of heating and cooling applied to the surrounding brain tissue;
  (g) to provide an interstitial brain probe apparatus that accommodates temporal changes in brain morphology;
  (h) to provide an interstitial brain probe apparatus that increases blood flow in brain tissue surrounding an infarction;
  (i) to provide an interstitial brain probe apparatus that significantly reduces the level of excitotoxins in a cerebral infarction and surrounding ischemic tissue;

DRAWING FIGURES

FIG. 3 shows the introducer sheath.

DESCRIPTION—FIGS. 1–7 PREFERRED OPERATIONAL EMBODIMENTS

Figure 1:
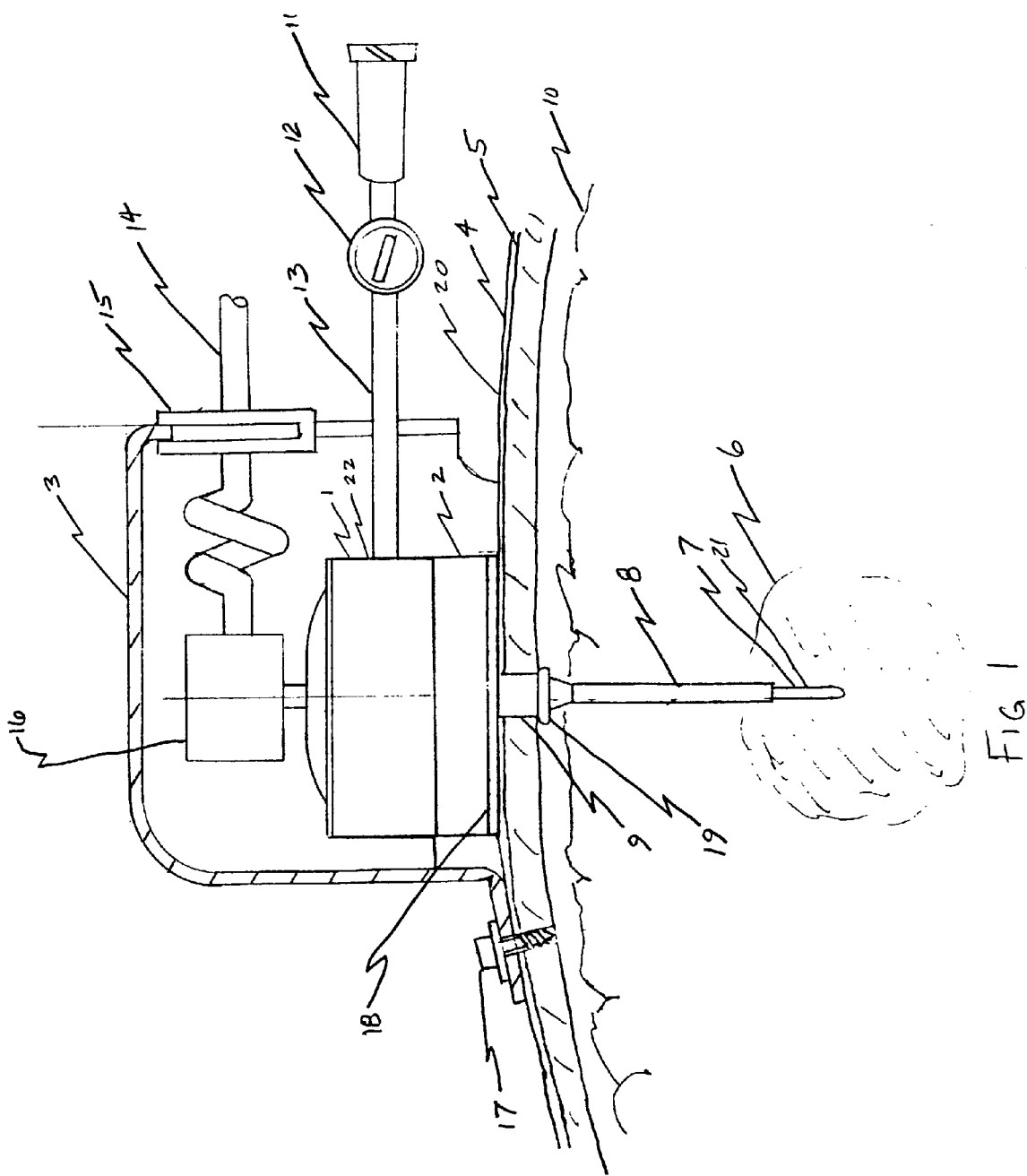
FIG. 1 shows a section of a human head with the interstitial brain probe and introducer sheath fixated to the head, and the distal tip of the interstitial brain probe placed into an infarction in the brain. The protective shield is also shown mounted to the head with screws.

FIG. 1 depicts, in simplified form, a section of the head with an interstitial brain probe 1 and introducer sheath 2 in operational position mounted on the head 20 with the distal end of the probe 7 centered in an infarcted zone of tissue 6. The protective shield 3 covers the interstitial probe/introducer sheath assembly 1 & 2 and is mounted to the head 20 with self-tapping bone screws 17. The shaft of the interstitial brain probe 21 passes through the introducer sheath tube 8 and connects the distal end of the probe 7 to the interstitial probe housing 22 and the manifold assembly 16. The interstitial probe/introducer sheath 1&2 is fixated to the head by outward expansion of the fixation plug 19 against the surgically created craniotomy hole 9 in the skin 4 and skull 5. The fixating plug as 19 seals the craniotomy hole 9 and prevents infection, providing for long term indwelling (greater than 1 hour and as long as two months) of the interstitial probe/introducer sheath assembly 1 & 2 in the brain 10. Antiseptic pad 18 provides further protection against infection. Fluid tube 13, stop cock 12, and luer fitting 11 provides fluid communication from the distal end of introducer sheath tube 8 and provides for aspiration of blood in case of hemorrhage within the infarction 6, and introduction of therapeutic substances into the infarction 6. The interstitial probe is connected to a control console by umbilical 14. The umbilical 14 is restrained by umbilical restraining block 15 and protective shield 3. The probe 1 provides for thermal coagulation of the infarction 6 and prolonged cooling of the infarction 6.

Figure 2:
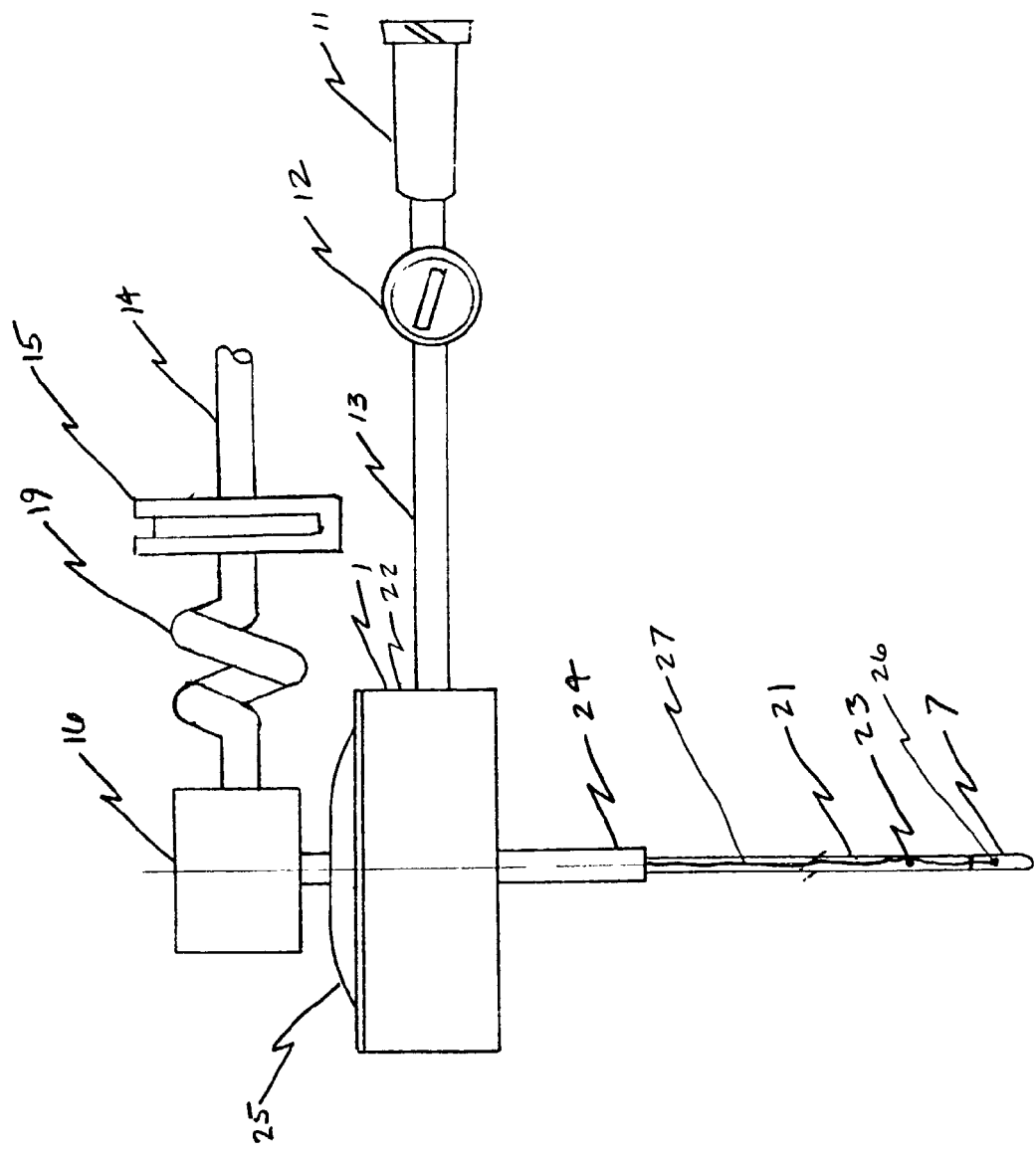
FIG. 2 shows the interstitial brain probe.

FIG. 2 depicts the interstitial brain probe 1. Interstitial probe shaft 21 connects the distal tip of the probe 7 to the manifold assembly 16 and passes through interstitial probe housing 22 and fixating plug expansion tube 24. The distal end of the interstitial brain probe 7 contains a mechanism for coagulating tissue surrounding the distal tip 7, and a mechanism for cooling the tissue surrounding the distal tip 7. The mechanism for coagulation is by monopolar radio frequency (RF) energy dissipation from the distal tip of the interstitial probe 7. A monopolar radio frequency electrode is formed at distal tip 7 by applying one pole of RF energy to of the entire length of probe shaft 21, with insulation sheath 23 covering the length of the shaft except distal end 7. Therefore the shaft is insulated, and only the distal tip 7 is electrified. Cooling of tissue surrounding the distal end of the shaft 7 is accomplished by Joule-Thompson effect where gas is expanded from high pressure to low pressure in the distal tip of the probe 7. Thermocouple 26 is welded to the distal tip 7 and is used to control the coagulation mode and the cooling mode of the probe. Thermocouple leads 27 pass under the insulation sheath 23 and are connected to the control console through umbilical 14. Umbilical 14 contains a high-pressure gas/RF conduit 28 (FIGS. 14 & 15), and thermocouple leads 27. The walls of the umbilical (FIGS. 14 & 15) provides low pressure gas return to the control console (not shown). Umbilical retaining block 15 mates with the protective shield 3 (FIGS. 1 & 4) and prevents injury to the patient in case of accidental pulling of the umbilical 14. Umbilical coil 19 allows for axial and lateral movement of the interstitial probe relative to the umbilical retaining block 15. Diaphragm 25 provides for axial displacement of the probe shaft 21 and the manifold assembly 16 relative to probe housing 22, and seals the assembly to prevent contamination and infection.

FIG. 3 depicts the introducer sheath 2. The introducer sheath is placed into the brain 10 through craniotomy hole 9 (FIGS. 1, 5, 6 & 7) with stereotaxic access needle 36 (FIG. 5) and the interstitial probe 1 is then placed into the brain 10 through the introducer sheath 2. The introducer sheath 2 provides for access to an infarction by standard stereotaxic surgical methods, and allows for removal and replacement of the interstitial probe 1 during the course of the treatment. The introducer sheath consists of sheath tube 8, housing 30, antiseptic pad 18, and interstitial probe docking pins 29. Fixation plug 19, and probe sealing boss 31 are formed integrally with the introducer housing 30. The fixation plug 19 works integrally with the interstitial probe 1 to fixate the assembly to the head, and seal the craniotomy hole 9. The probe sealing boss 31 mates with the bottom surface of the interstitial probe 1 and seals the assembly to prevent contamination and infection.

Figure 4B:
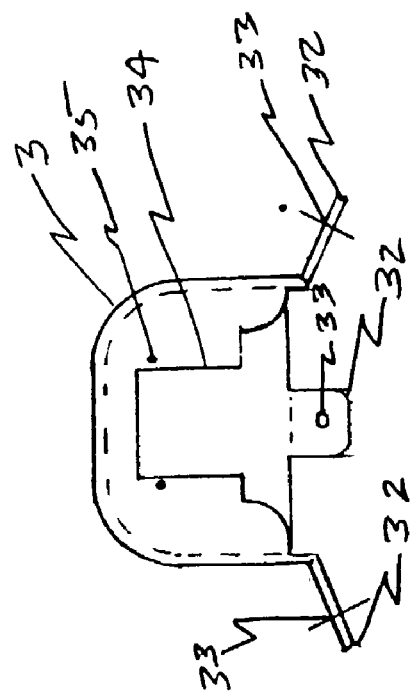
FIG. 4 shows the protective shield.
Figure 4A:
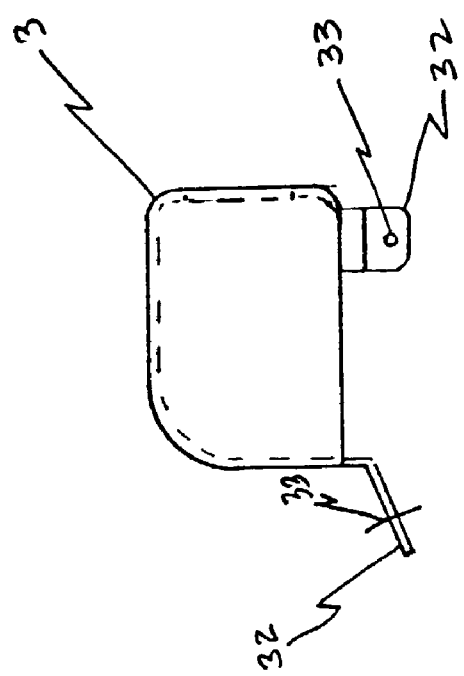

FIG. 4A depicts a side view of protective shield 3. FIG. 4B depicts a front view of protective shield 3. The protective shield 3 is injection molded from a suitable plastic such as nylon. Mounting tabs 32, and screw holes 33 provide for mounting of the protective shield 3 to the head 20 with self tapping bone screws 17 (FIG. 1) which fasten to the skull 5. Umbilical retaining block cutout 34 retains the umbilical retaining block 15 (FIGS. 1, 2 & 15) by a tongue and groove mechanism. Detents 35 allow for a "snap fit" with the umbilical retaining block 15.

Figure 5:
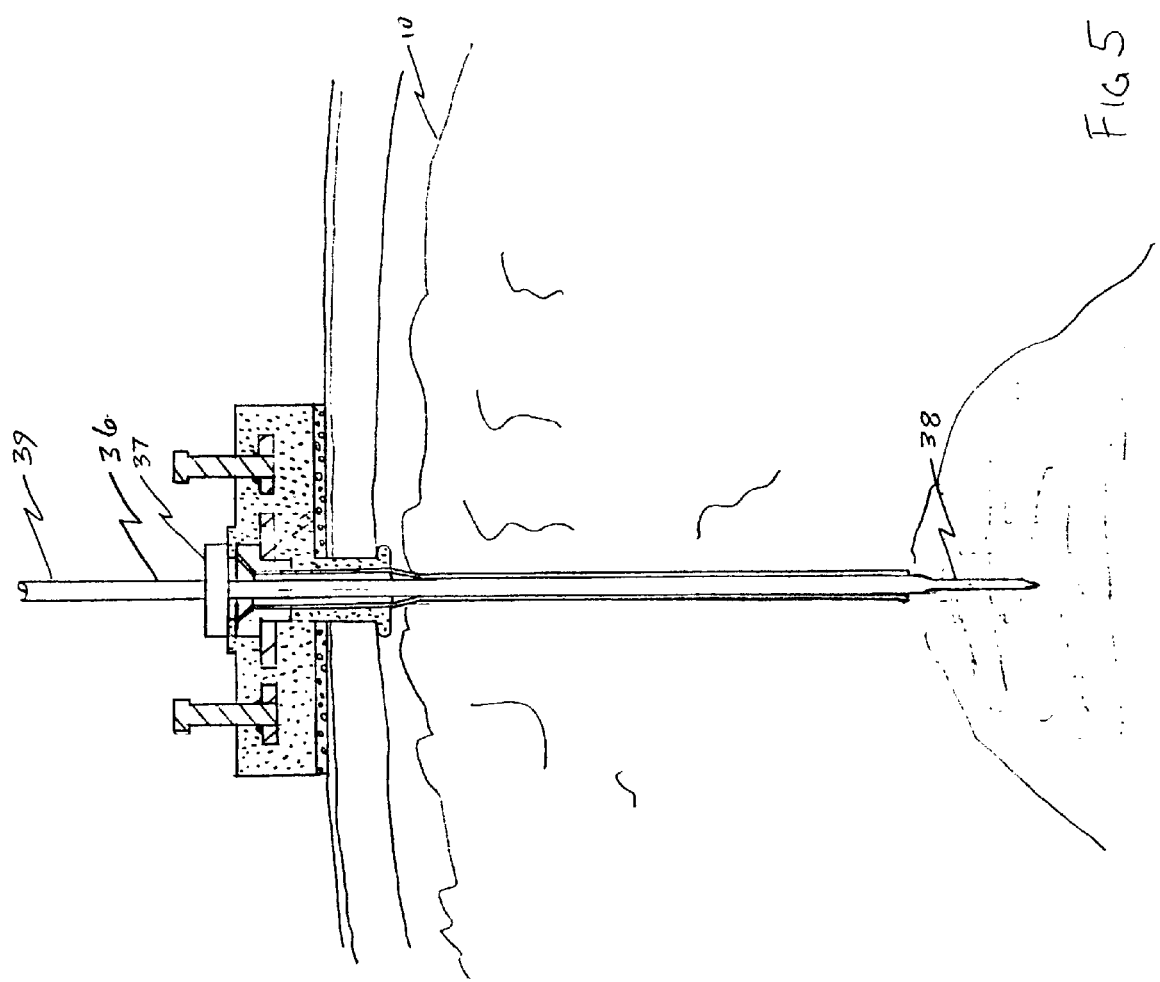
FIG. 5 shows a sectional view of the introducer sheath placed into position with a stereotaxic access needle through a craniotomy.
Figure 6:
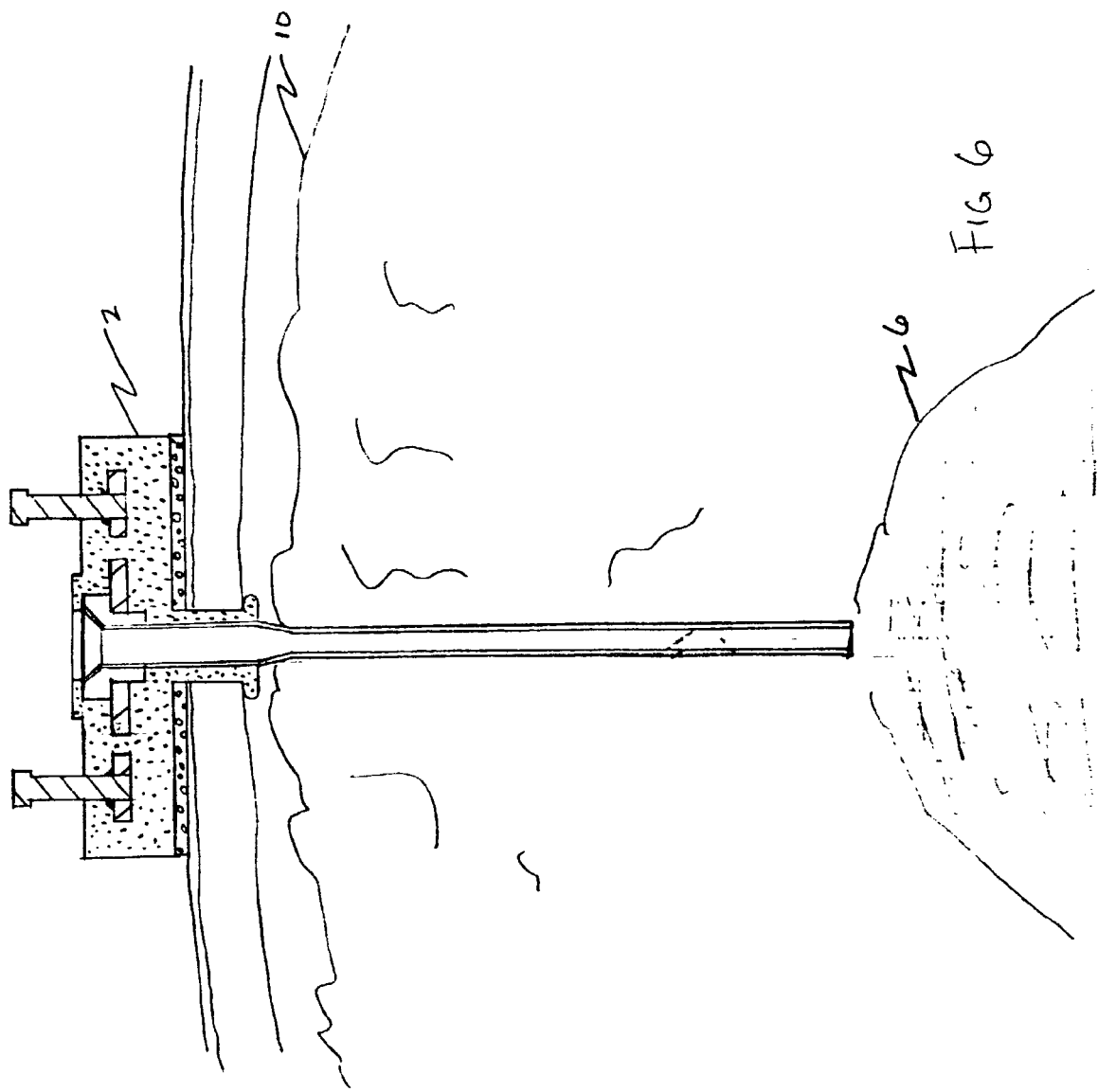
FIG. 6 shows a sectional view of the of the introducer sheath in position after the stereotaxic access needle is removed.

FIG. 5 depicts introducer sheath 2 placement into the brain 10 with the stereotaxic access needle 36. Stereotaxic access needle 36 is sized to protrude past the introducer tube a distance that is equivalent to the distance the interstitial probe shaft 21 protrudes past the introduce tube (Approximately 1 cm). The diameter of the introducer needle is tapered at the distal tip to the diameter of the interstitial probe shaft 21 as shown. Proximal to the taper, the diameter of the stereotaxic needle is sized to slidably fit the inside diameter of the introducer tube 8. Needle stop 37 pushes the introducer sheath into the brain 10 when the stereotaxic access needle 36 is advanced. The proximal end of the stereotaxic access needle 39 is configured to function with various commercial stereotaxic needle guidance systems (not shown). FIG. 6 depicts the introducer sheath 2 in the brain 10 after the stereotaxic access needle 36 (FIG. 5) is removed.

Figure 7:
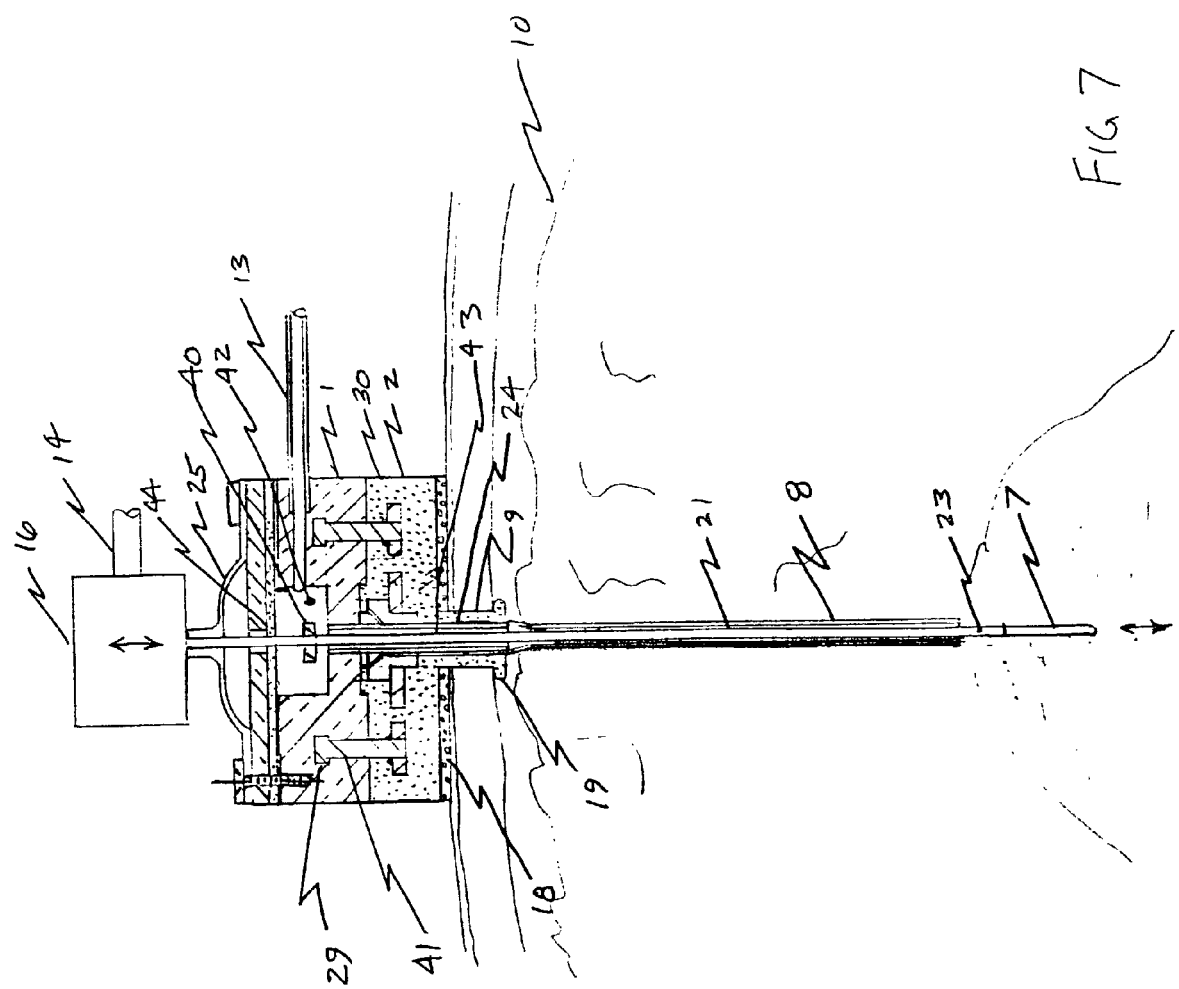
FIG. 7 shows a sectional view of the interstitial brain probe and introducer sheath in position with the distal tip of the interstitial brain probe located at about the center of an infarction.
Figure 9B:
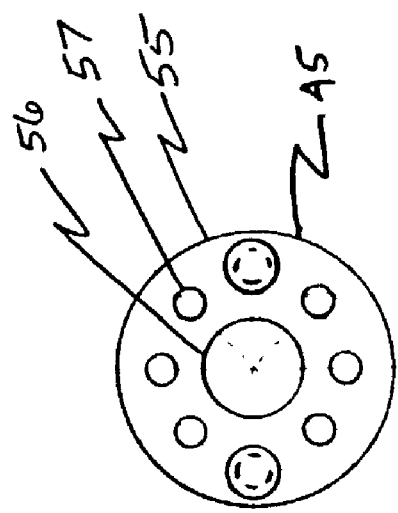
FIG. 9B shows a top view of the sheath probe docking ring.

FIG. 7 depicts in sectional view the interstitial probe 1 and introducer sheath 2 assembled in treatment position. After the stereotaxic access needle 36 is removed from the introducer sheath 2 the interstitial probe 1 is inserted into the introducer sheath 2 and locked together by docking pins 29 into docking ways 41 (See FIGS. 9 & 12 for construction details). The fixating plug expansion tube 24 of the interstitial probe 1 is sized to expand the walls of fixation plug 19 when the interstitial probe is assembled to the introducer sheath sufficiently to hermetically seal the craniotomy hole 9 by outward expansion of the fixating plug. This mechanism also provides for a fluid tight seal between the inner wall of the introducer sheath tube 8 and the outer wall of fixation plug expansion tube 24. A fluid communication pathway 43 is therefore formed from the fluid chamber 42 in the interstitial probe to the distal end of introduce sheath tube 8 by the space between the inner wall of the introducer sheath tube 8 and fixation plug expansion tube 24 as shown. Blood may be aspirated from the distal end of introducer sheath tube 8 by applying suction to fluid tube 13, or, a therapeutic substance may be introduced into the brain 10 by injecting the therapeutic substance through fluid tube 13. The interstitial probe shaft 21 and the manifold assembly 16 has freedom of movement in the axial direction relative to the interstitial probe housing 22 and the introducer sheath 2. Axial movement of the interstitial probe shaft 21 and the manifold assembly 16 is limited by travel stop 40. (Following stroke, the brain swells. When the brain is cooled with the interstitial probe, brain swelling will be reduced, and the brain will shrink causing an axial force on the probe. Axial movement of the interstitial probe shaft is of critical importance since tissue surrounding the distal tip of the probe is frozen to the distal tip of the probe during the cooling phase of the treatment. By allowing the probe to move in an axial direction as the brain shrinks, trauma to the tissue at the distal end of the probe, and associated hemorrhage will be avoided.) gasket 44 seals the interstitial probe shaft 21 from fluid in the fluid chamber 42.

DESCRIPTION FIGS. 8–15—PREFERRED CONSTRUCTION EMBODIMENTS

Figure 8:
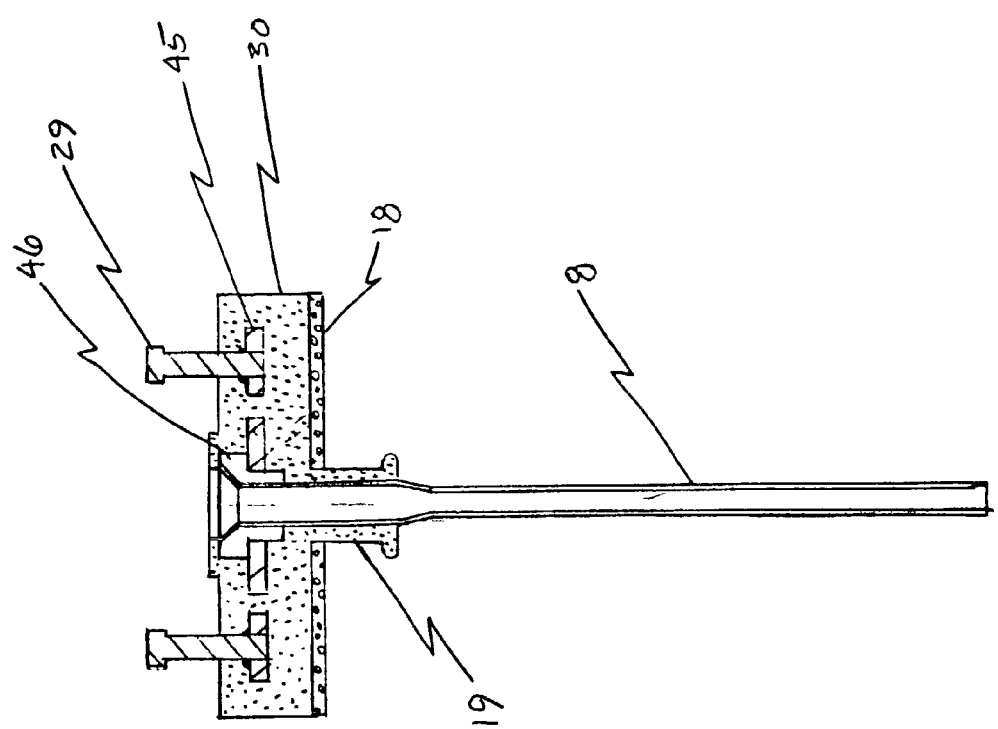
FIG. 8 shows a sectional view of the construction of the introducer sheath.

FIG. 8 depicts a sectional view of the introducer sheath 2. The introducer sheath consists of the sheath/probe docking ring assembly 45 (See FIG. 9 for construction details), introducer sheath tube assembly 46 (See FIG. 10 for construction details) Antiseptic pad 18, and introducer sheath housing 30. The introducer sheath assembly, except the antiseptic pad is formed by placing the sheath/probe docking ring assembly 45, and introducer sheath tube assembly 46 into a fixturing mold and casting the introducer sheath housing 30 to form the integrated assembly. The introducer sheath housing 30 is cast from a two-part medical grade silicon rubber with a hardness of between 40 and 60 durometer. Dow-Corning Corporation manufactures a full line of medical grade silicon rubber suitable for this application. The antiseptic pad 18 is made from open cell foam, and is saturated with antiseptic fluid either at the factory, or in the field prior to use. The foam is between 10 and 20 durometer in hardness. A suitable antiseptic fluid is an iodine solution marketed under the registered trade name Betadine. The foam pad 18 may be glued to the bottom face of the introducer housing 30 with a suitable adhesive.

Figure 9A:
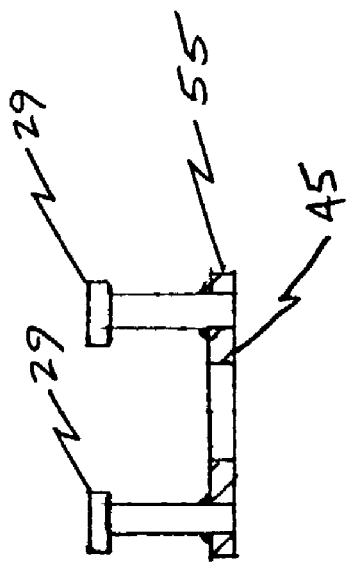
FIG. 9A shows a sectional view of the sheath/probe docking ring.

FIG. 9A shows a sectional view of the sheath/probe docking ring assembly 45. The sheath/probe docking ring assembly 45 consists of type 304 stainless steel docking ring 55 and two type 304 docking pins 29. The docking ring 55 has a hole in the center which mates with the sheath tube assembly 46 as shown in FIG. 8. The docking ring has (6) holes 57 which provide anchorage within the introducer sheath housing 30 when the introducer sheath housing is molded around the sheath/probe docking assembly. The docking pins 29 are welded to the docking ring 56.

Figure 10:
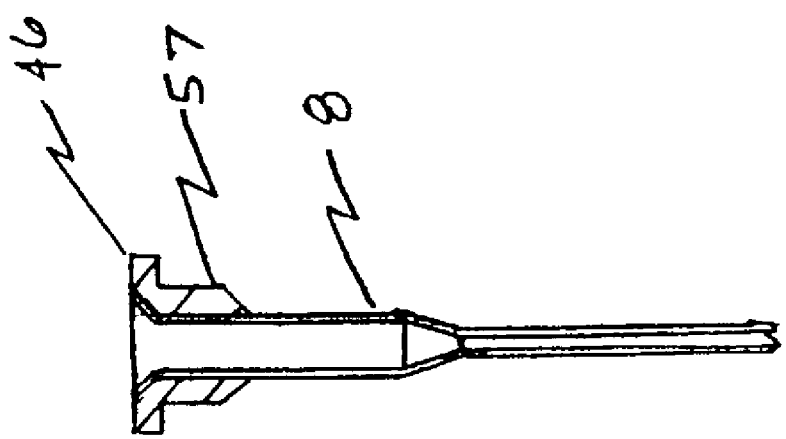
FIG. 10 shows a sectional view of the construction of the sheath tube.

FIG. 10 shows a sectional view of the introducer sheath tube assembly 46. The introducer sheath tube assembly 46 consists of the sheath tube 8, and the sheath ferrule 57. The sheath tube 8 and the sheath ferrule 57 are made of high density polyethylene or other suitable thermoplastic. The sheath tube is extruded into tubular form by standard means, and then blow molded into final shape. The wall thickness of the sheath tube is between 0.001 and 0.002 inches. The inside diameter of the sheath tube at the distal end is 0.020 to 0.025 inches greater than the diameter of the interstitial probe shaft 21 it is designed to mate with. The inside diameter of the sheath tube at the proximal end is 0.001 to 0.004 inches smaller than the fixation plug expansion tube 24 on the interstitial probe that it is designed to mate with. The sheath ferrule 57 is injection molded and is bonded to sheath tube 8 by standard ultrasonic welding techniques.

Figure 11:
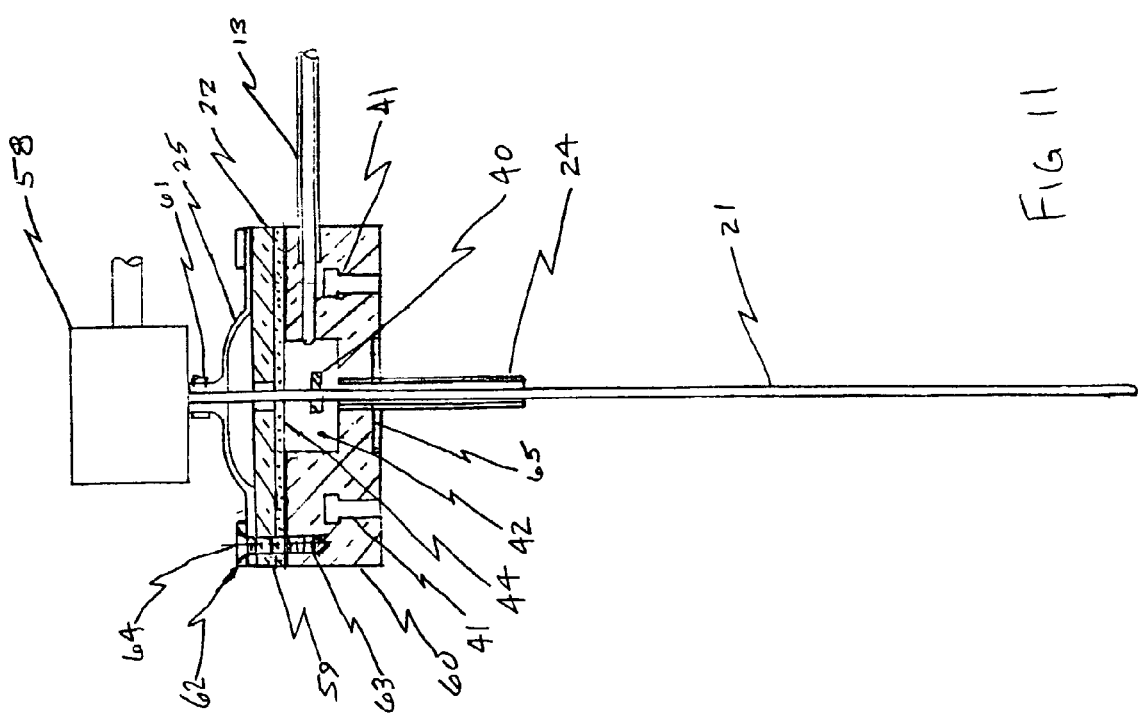
FIG. 11 shows a sectional view of the construction of the interstitial probe housing.
Figure 14:
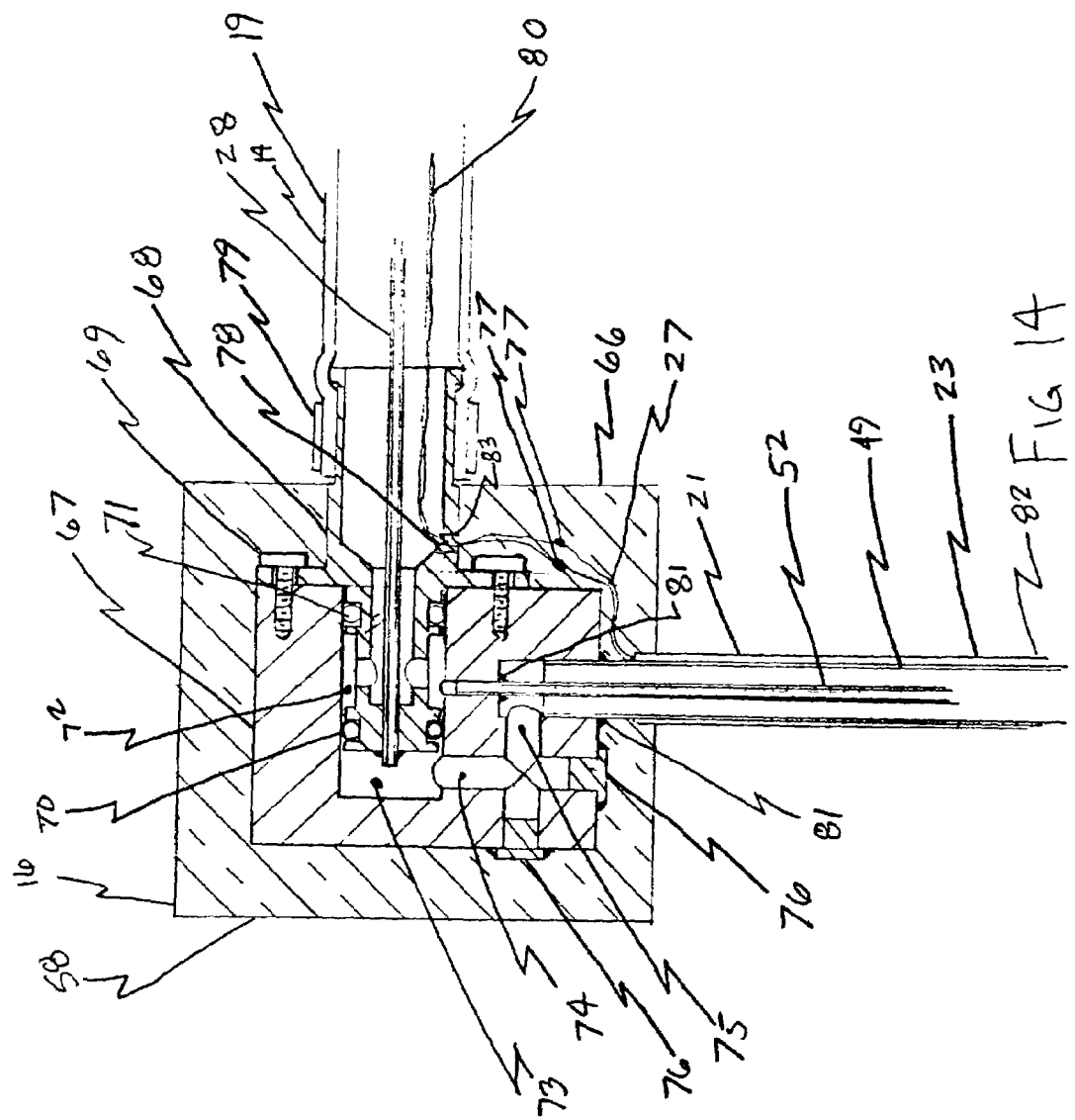
FIG. 14 shows a sectional view of the construction of the proximal end of the interstitial probe depicting the gas manifold and umbilical attachment.

FIG. 11 shows a sectional view the interstitial probe housing assembly 22 assembled with interstitial probe assembly 58 (FIG. 14). The interstitial probe housing assembly consists of upper housing 59, lower housing 60, diaphragm 25, diaphragm crimp ring 61, diaphragm retaining ring 62, gasket 44, fixation plug expansion tube 24, travel stop 40, fluid tube 13, and (6) flat head machine screws 64. Upper housing 59 and lower housing 60 are formed of a machineable grade of nylon by injection molding. Fixation plug expansion tube 24 and fluid tube 13 are insert molded into lower housing 60 during the molding process. Docking pin ways 41 and thread tap 63 are machined into the lower housing 60 after the molding process. Fluid chamber 42, and boss relief 65 are formed during the molding process. Travel stop 40, diaphragm retaining ring 62, diaphragm crimp ring 61 are type 304 stainless steel. Gasket 42 is molded out of medical grade silicone rubber and has a durometer of 40 to 60. Machine screw 64 is type 304 stainless steel. The outside diameter of the housing assembly is 0.750 to 0.875 inches. Other dimensions are proportional as shown. The assembly process consists of: 1.) Diaphragm 25 is crimped to the interstitial probe assembly shaft 21 with diaphragm crimp ring 61. 2.) Upper housing 59 is slid over the interstitial probe assembly shaft 21. 3.) Gasket 44 is slid over the interstitial probe assembly shaft 21. 4.) Travel stop 40 is crimped to the interstitial probe assembly shaft 21. 5.) Lower housing 60 is slid over the interstitial probe assembly shaft. 6.) Assembly is bolted together with (Qty. 6) machine screws 64 and diaphragm retaining ring 62.

Figure 12:
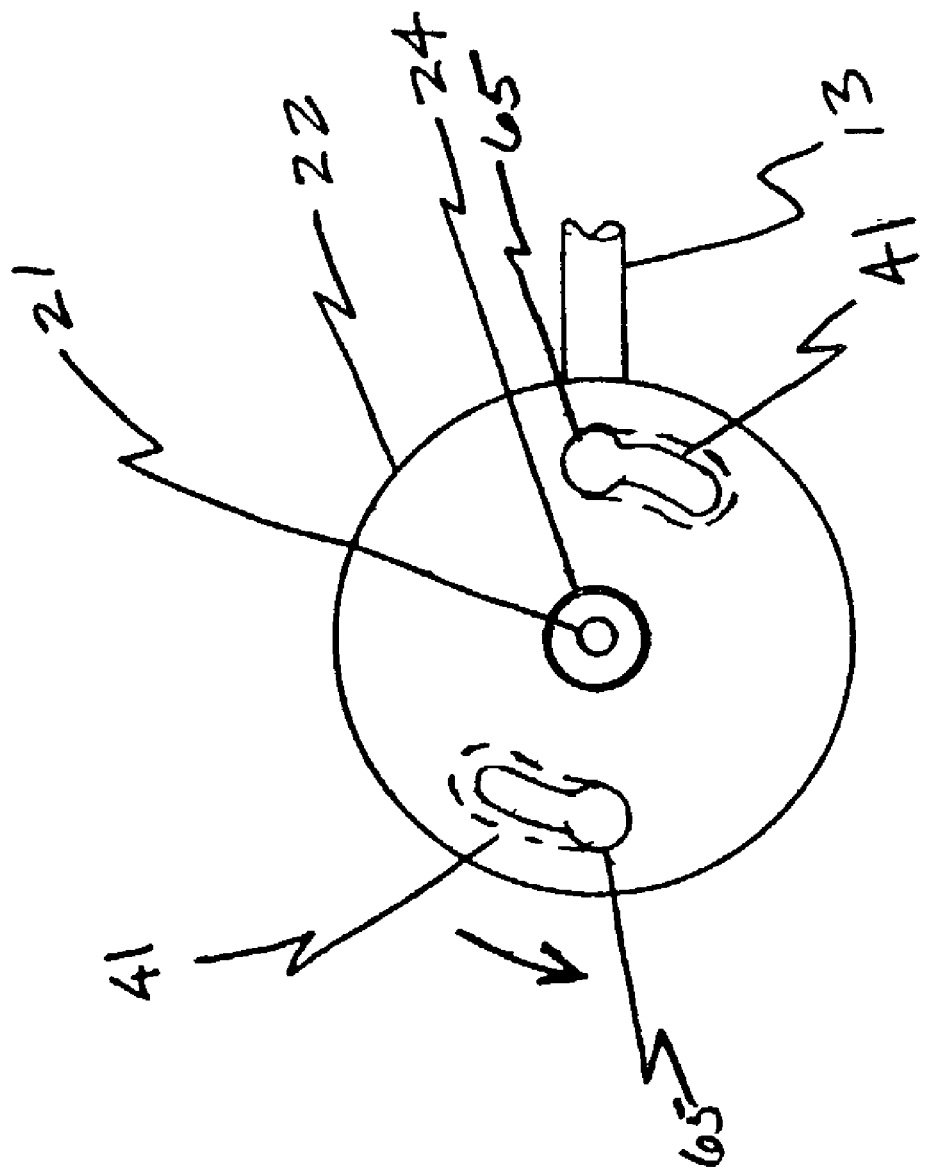
FIG. 12 shows a bottom view of the interstitial probe housing depicting the probe/sheath docking mechanism.

FIG. 12 shows a bottom view of the interstitial probe 1 depicting the sheath/housing docking mechanism. Introducer sheath docking pins 29 (FIG. 8) enter pinhole 65. The interstitial probe is then rotated 45 degrees in the direction shown to lock the interstitial probe 1 to introducer sheath 2.

Figure 13:
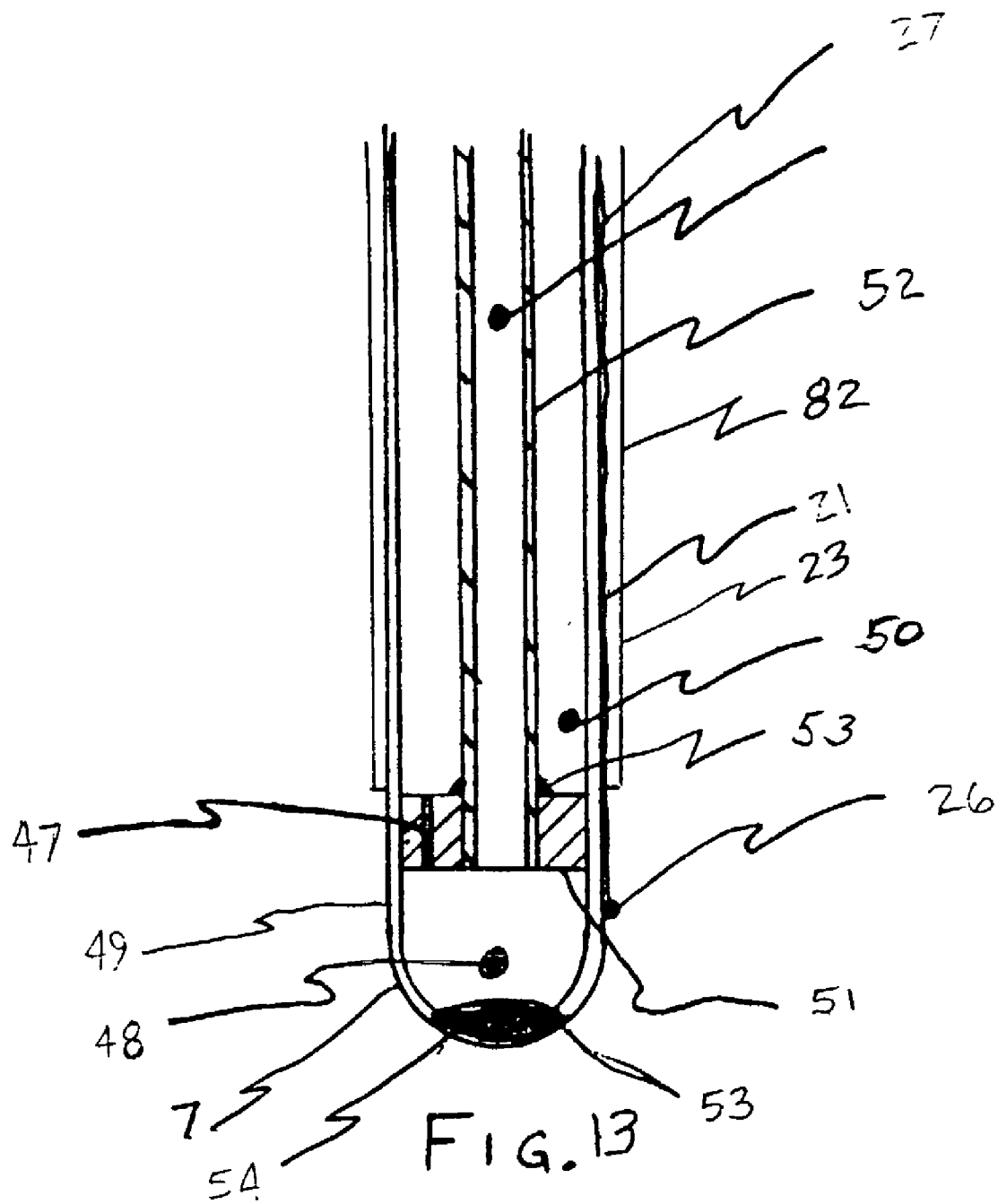
FIG. 13 shows a sectional view of the construction of the distal end of the interstitial probe shaft depicting the cooling and heating mechanisms.

FIG. 13 shows a sectional view of the distal tip 7 of the interstitial probe depicting the heating mechanism and the cooling mechanism of the probe. The preferred cooling mechanism is by Joule-Thompson effect where gas at high pressure is expanded through a restriction 47 to an expansion chamber 48 at low pressure. The expansion causes the gas to loose heat causing a reduction in temperature of the gas, and significant cooling of the walls of the expansion chamber 49. Gas is supplied at high pressure from the control console through high pressure tube 28 (FIGS. 14 & 15) contained in the umbilical cable 14 into the high pressure chamber 50 in the probe shaft 21. The gas at high pressure is metered into the expansion chamber 48, which is at low pressure through a restriction 47 in the pressure bulkhead 51. Gas is exhausted from the expansion chamber through low-pressure tube 52 and returned to the control consol through umbilical 14. The preferred gasses are nitrogen, or argon, or a mix of argon and nitrogen due to their thermodynamic properties, and their inertness. The pressure of the gas supplied to the tip is between 200 psi and 1500 psi. In addition to the cooling mechanism described above, FIG. 6 shows a thermocouple 26 welded to the exterior surface of the expansion chamber. The thermocouple 26 is used to control temperature of the wall of the expansion chamber 11 during the coagulation mode, and during the cooling mode.

The leads of the thermocouple 27 are bonded to the probe shaft 21 with adhesive, and run under insulation sheath 23 and extend into the manifold assembly (FIG. 14) of the interstitial probe 1 and through the umbilical cable 14 and are connected to circuitry in the control console (not shown). The shaft 21 and expansion chamber 48 are formed by a type 304 stainless steel tube with an outside diameter between 1 mm and 2 mm, and a wall thickness of 0.002 inches to 0.004 inches. The expansion chamber 48 is formed from shaft 21 by a common forging process called swaging. The tip of the expansion chamber 53 is closed by silver solder 54. The probe tip 7 is than ground and polished to provide a smooth spherical end. The low-pressure tube 52 is made of type 304 stainless steel and is between 0.5 mm and 1.25 mm in diameter with a wall thickness of about 0.002 inches. The pressure bulkhead 51 is machined from type 304 stainless steel and is attached to the low pressure tube by silver solder 54. The restriction 47 is between 0.002 and 0.008 inches in diameter and is accomplished by electron discharge machining commonly know as EDM. The pressure bulkhead is press fit into the shaft 21 after the low-pressure tube 52 is attached to the pressure bulkhead 22, and before the expansion chamber 48 if formed and sealed. The shaft 21 is electrified with one pole of RF energy. The insulating sheath 23 electrically isolates the shaft except at the distal end 7 thereby forming an electrode at the distal end 7.

FIG. 14 shows a sectional view of the proximal end of interstitial probe assembly 58. The interstitial probe assembly consists of housing 66, probe needle assembly 82, manifold 67, umbilical assembly 14, housing 66, umbilical retaining screws 69, hole plugs 76, and silver solder 81. The umbilical assembly consists of coaxial pressure fitting 68, O-ring 70, O-ring 71, high-pressure tube 28, thermocouple leads 80, low pressure tube strap 79, umbilical retaining block assembly 15 (FIG. 15), and control console connecter plug (not shown or disclosed). Probe needle assembly 82 (FIG. 13) consists of low pressure tube 52, high pressure tube 49, insulation sleeve 23, thermocouple leads 27, thermocouple 26 (FIG. 13), pressure bulkhead 51 (FIG. 13), and silver solder 53 (FIG. 13). The manifold 67, and pressure fitting 68 are machined out of Type 304 stainless steel. High-pressure tube 28 is made of a nickel-titanium alloy marketed under the trade name Nitonol. High-pressure tube 28 supplies high-pressure gas from the control console (not shown) to the manifold 67. High pressure gas leaves high-pressure tube 28 and enters high pressure chamber 73 in manifold 67, then travels through holes 74 and 75, then enters high-pressure tube 49 of the probe needle assembly 82, then is expanded through orifice 47 into low-pressure chamber 48 (FIG. 13). Hole plugs 76 are welded into place after manifold 67 machining to seal holes 74 and 75. O-ring 70 of the umbilical assemble separates high-pressure chamber 73 from low-pressure chamber 72 in the manifold 67. Gas is returned to the manifold 67 from low-pressure chamber 48 (FIG. 13) by low-pressure tube 52 of the probe needle assembly 82. Gas leaves low-pressure tube 52 of the probe needle assembly 82 and enters low-pressure chamber 72, and is returned to the control console by umbilical tube 19. Umbilical tube 19 is fixated to pressure fitting 68 by stainless steel hose clamp 79. O-ring 71 seals low-pressure chamber 72 from ambient air. RF energy is conducted from the control console (not shown) to the manifold 67 and probe needle assembly 82 by high-pressure tube 28 of the umbilical assembly. Signals from thermocouple 26 (FIG. 13) and thermocouple leads 27, are sent to the control console (not shown) via thermocouple leads 80 of the umbilical assembly 82. Thermocouple leads 80 exits pressure fitting 68 at hole 78, and the hole 78 is sealed with silicon rubber compound 83. Dow Corning Corp. manufactures a complete line of silicone rubber sealing compounds suitable for this application. Probe needle assembly is soldered to manifold with silver solder 81 by standard induction heating means. After umbilical assembly 14 is fastened to manifold 67 with stainless steel machine screws 69, thermocouple leads 27 are connected to thermocouple leads 80 by spot welding. Silicone rubber compound 77 is applied to thermocouple lead weld joints to provide electrical insulation. Housing 66 is formed by insert molding around the assembly as shown. Housing 66 is made from a suitable thermoplastic such as nylon, or polycarbonate.

Figure 15:
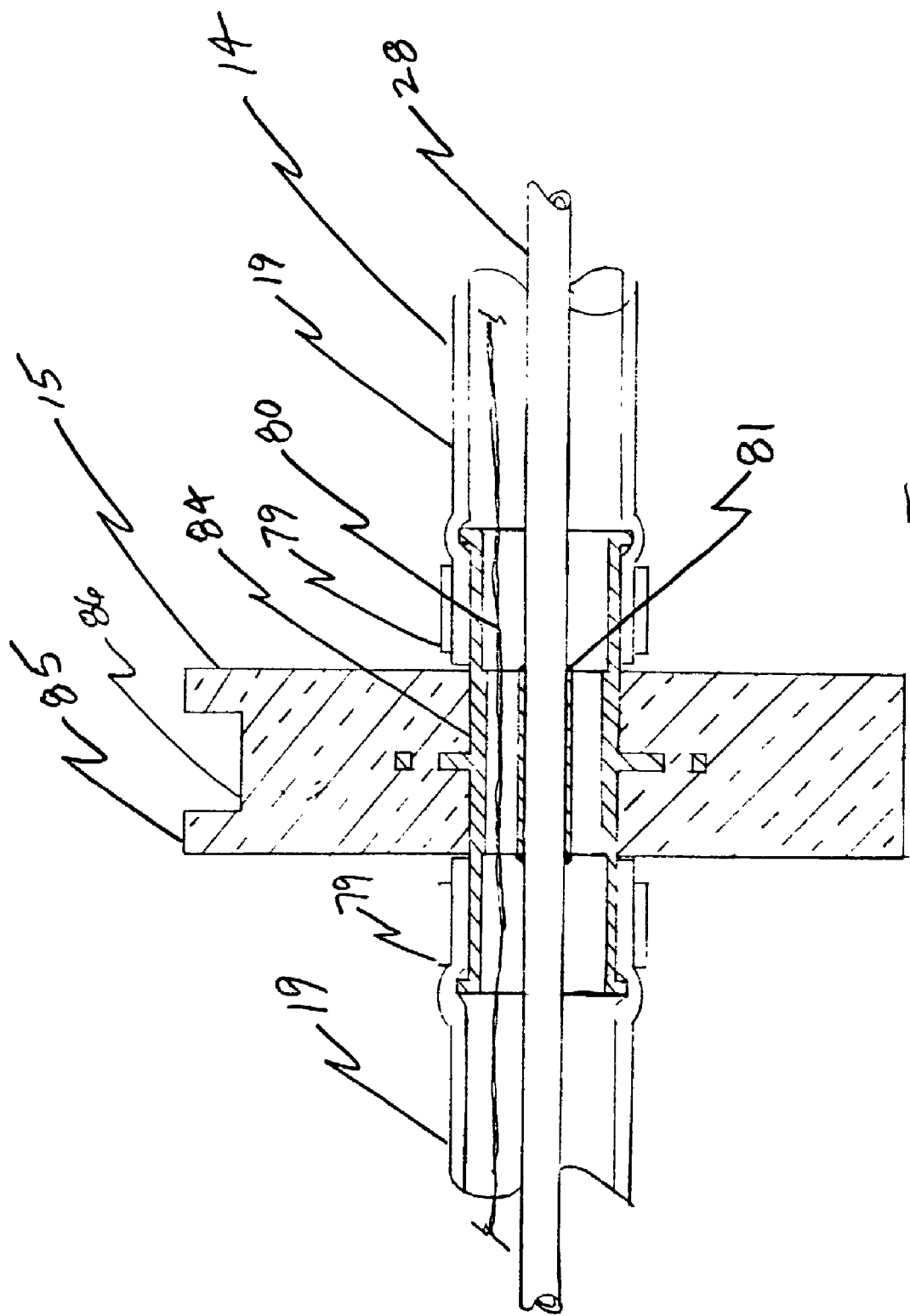
FIG. 15 shows a sectional view of the construction of the umbilical retaining block assembly.

FIG. 15 shows a sectional of the umbilical retaining block assembly 15 (FIGS. 1 & 2). The umbilical retaining block assembly 15 is a sub-assembly of umbilical assembly 14. The umbilical retaining block assembly 15 mates with protective shield 3 (FIG. 1) to retain the umbilical. High-pressure tube 28 is soldered to umbilical flange 84 with silver solder 81 as shown. Thermocouple lead 80 traverses umbilical flange 84 through one of several holes drilled through the flange. Low-pressure umbilical tube 19 is fixated to both ends of umbilical flange 84 with stainless steel hose clamps 79. Low-pressure tube 19 is made of nylon and is approximately 0.250 inches in inner diameter, and has a wall thickness of approximately 0.015 inches. Umbilical flange housing 85 in insert molded around umbilical flange 84 and is made of a suitable thermoplastic material such as nylon or polycarbonate. Groove 86 is formed during the molding process, and mates with protective shield 3 (FIG. 1) to retain the umbilical.

ADVANTAGES

From the description above there are a number of advantages my apparatus for treating stroke provide:

(a) An interstitial probe apparatus may be practically placed into a cerebral infarction through a small diameter craniotomy burr hole by standard stereotaxic means, and provide coagulation of infarcted brain tissue to reduce the risk of hemorrhage, and provide for and an extended period of local cerebral hypothermia to increase blood flow in brain tissue surrounding the infarction, while simultaneously reducing the level of excitotoxins;

(b) Blood may be aspirated from within the cerebral infarction without removing the interstitial probe;

(c) Therapeutic substances may be delivered into the cerebral infarction without removing the interstitial probe;

(d) The brain may contract or expand with the interstitial probe apparatus in place and functioning without causing trauma to the brain;

(e) The interstitial probe apparatus hermetically seals the craniotomy to prevent infection thereby providing for practical long term indwelling of the interstitial probe in the brain;

(f) The interstitial probe apparatus provides protection against patient injury in case of inadvertent or accidental pulling of the probe umbilical;

I claim:

1. A method for reducing secondary ischemic brain injury comprising the steps of:
  (a) placing a probe into an ischemic region of the brain;
  (b) heating at least a portion of said ischemic region with said probe to cause coagulation of at least some portion of said ischemic region;
  (c) cooling at least a portion of said ischemic region with said probe for a period of tire greater than one hour, and less an one month;
  (d) removing said probe from said brain.

2. The method of claim 1 wherein said cooling results in at least some portion of said ischemic region being at a temperature below zero degrees centigrade for a period of time greater than one hour, and less than one month.

3. The method of claim 1 wherein said probe is placed into said ischemic region where said ischemic region comprises brain tissue that has been irreversibly injured.

4. The method of claim 1 wherein said heating and cooling is substantially limited to said ischemic region.

5. An interstitial brain heating/cooling probe comprising:
  (a) an elongated structure which includes a distal end, and a proximal end;
  (b) a heating means located in the vicinity of said distal end, the heating means configured to coagulate at least a portion of an ischemic region of a brain;
  (c) a cooling means located in the vicinity of said distal end, the cooling means configured to induce hypothermia within at least a portion of an ischemic region of a brain;
  (d) a means in the vicinity of said proximal end for fixating said interstitial brain heating/cooling probe to a head;
  (e) a means of connecting said brain heating/cooling probe to a source of heating energy, and a source of cooling fluid; and
  (f) a probe housing having a diaphragm, the proximal end of the elongated structure coupled to the diaphragm such that a long axis of the elongated structure orients substantially perpendicular to the diaphragm, the diaphragm providing axial displacement of the elongated structure relative to the probe housing.

6. The interstitial brain heating/cooling probe of claim 5 wherein said elongated structure is sized and shaped such that said distal end may be slidably placed into an ischemic region of the brain through an introducer sheath.

7. The interstitial brain heating/cooling probe of claim 5 includes a physiological sensor located in the vicinity of said distal end.

8. The interstitial brain heating/cooling probe of claim 7 wherein said physiological sensor is a temperature sensor.

9. The interstitial brain heating/cooling probe of claim 5 wherein said heating means is provided by mono-polar dissipation of radio frequency energy.

10. The interstitial brain heating/cooling probe of claim 5 wherein said cooling means is provided by Joule-Thompson effect.

11. The interstitial brain heating/cooling probe of claim 5 wherein said cooling means is provided by evaporation of liquid refrigerant.

12. The interstitial brain heating/cooling probe of claim 5 wherein said means of fixating said interstitial brain-cooling probe to the head provides for brain cooling for a period of time greater than one hour, and less than one month.

13. The interstitial brain heating/cooling probe of claim 5 wherein said means of connecting said interstitial brain heating/cooling probe to said source of heating energy and said source of cooling fluid comprises an umbilical where said umbilical includes at least one electrical conduit and at least one cooling fluid conduit.

14. The interstitial brain heating/cooling probe of claim 13 wherein the axis of said umbilical is approximately perpendicular to the axis of said interstitial brain heating/cooling probe at the point of connection to said interstitial brain heating/cooling probe.

15. The interstitial brain heating/cooling probe of claim 5 comprising a sheath coupled to the proximal end of the elongated structure, the sheath having a sheath tube extending about the elongated structure from the proximal and of the elongated structure to the distal end of the elongated structure, the sheath tube defining a fluid communication pathway between an inner wall of the sheath tube and the elongated structure, the fluid communication pathway configured to allow fluid flow between a distal end of the interstitial probe and a proximal end of the interstitial probe.

16. Apparatus for reducing secondary ischemic brain injury comprising:
    (a) an interstitial brain heating/cooling probe;
    (b) an introducer sheath;
    (c) a control console;
    wherein said interstitial brain heating/cooling probe comprises an elongated structure which includes a distal end, and a proximal end whereby a heating means and a cooling means are provided in the vicinity of the distal end, and whereby said interstitial brain heating/cooling probe is sized and shaped such that said distal end may be slidably placed into an ischemic region of the brain through the introducer sheath, the heating means is configured to coagulate at least a portion of an ischemic region of a brain and the cooling means configured to induce hypothermia within at least a portion of an ischemic region of the brain;
    wherein said interstitial brain heating/cooling probe comprises a probe housing having a diaphragm, the proximal end of the elongated structure coupled to the diaphragm such that a long axis of the elongated structure orients substantially perpendicular to the diaphragm, the diaphragm providing axial displacement of the elongated structure relative to the probe housing; and
    wherein the said control console comprises a source of heating energy for said interstitial brain heating/cooling probe, and a source of cooling fluid for said interstitial brain heating/cooling probe, and a means to control the heating of the brain by said interstitial brain heating/cooling probe, and a means to control the cooling of the brain by said interstitial brain heating/cooling probe whereby said interstitial brain heating/cooling probe includes a means to connect said interstitial brain heating/cooling probe to said control console.

17. The introducer sheath of claim 16 wherein said introducer sheath comprises an elongated structure consisting of a distal end and a proximal end whereby said distal end is constructed for placement into an ischemic region of the brain by standard stereotaxic surgical technique, and whereby said proximal end comprises a means of sealing a craniotomy hole, and a means of preventing infection, and where said introducer sheath is constructed to slidably receive the interstitial brain heating/cooling probe of claim 16 after said introducer sheath is placed into said ischemic region of said brain.

18. The introducer sheath of claim 17 wherein said introducer sheath includes a fluid path from said distal end to said proximal end, where said proximal end includes a fluid port to said fluid path, where said fluid port and said fluid path may be used to remove blood clots from the brain, or said fluid port and said fluid path my be used to introduce therapeutic agents into the brain.

19. The apparatus of claim 16 wherein the sheath couples to the proximal end of the elongated structure, the sheath having a sheath tube extending about the elongated structure from the proximal end of the elongated structure to the distal end of the elongated structure, the sheath tube defining a fluid communication pathway between an inner wall of the sheath tube and the elongated structure, the fluid communication pathway configured to allow fluid flow between a distal end of the interstitial probe and a proximal end of the interstitial probe.

20. An interstitial probe comprising:
    a shaft having a proximal end and a distal end, the distal end of the shaft configured to position within an infarcted zone of tissue;
    a cooling mechanism oriented at the distal end of the shaft the cooling mechanism configured to induce hypothermia within at least a portion of the infarcted zone of tissue;
    a coagulation mechanism oriented at the distal end of the shaft; and
    a probe housing having a diaphragm, the proximal end of the shaft coupled to the diaphragm such that a long axis of the shaft orients substantially perpendicular to the diaphragm, the diaphragm providing axial displacement of the shaft relative to the probe housing.

21. The interstitial probe of claim 20 wherein the interstitial probe comprises a sheath having a sheath housing and a sheath tube coupled to the sheath housing, the sheath housing coupled to a probe housing associated with the proximal end of the shaft and the sheath tube extending about the shaft from the proximal end of the shaft to the distal end of the shaft, the sheath configured to insert within the infracted zone of tissue.

22. The interstitial probe of claim 21 wherein a space between an inner wall of the sheath tube and the shaft defines a fluid communication pathway, the fluid communication pathway configured to allow fluid flow between a distal end of the interstitial probe and a proximal end of the interstitial probe.

23. The interstitial probe of claim 21 wherein the sheath comprises a fixation plug oriented at a proximal end of the sheath tube, the fixation plug configured to expand against a surgical opening formed with a tissue to seal the surgical opening.

24. The interstitial probe of claim 23 wherein the interstitial probe further comprises a fixating plug expansion tube oriented at the distal end of the shaft, the fixating plug expansion tube configured to insert within the fixation plug of the sheath and expand the fixation plug against the surgical opening to seal the surgical opening.

25. The interstitial probe of claim 21 wherein the sheath housing comprises a pad having an antiseptic fluid, the pad oriented between the sheath housing and tissue of a surgical location.

26. The interstitial probe of claim 20 further comprising:
    an umbilical in communication with the cooling mechanism and in communication with the coagulation mechanism, the umbilical having an umbilical retaining block; and
    a shield coupled to a tissue of a surgical location and in communication with the umbilical retaining block of the umbilical.

27. An apparatus for inducing hypothermia comprising:
    a control console; and
    an interstitial probe coupled to the control console, the interstitial probe having:
        a shaft having a proximal end and a distal end, the distal end of the shaft configured to position within an infarcted zone of tissue;
        a cooling mechanism oriented at the distal end of the shaft, the cooling mechanism in fluid communication with the control console and configured to induce hypothermia within at least a portion of the infarcted zone of tissue;

a coagulation mechanism oriented at the distal end of the shaft, the coagulation mechanism in electrical communication with the control console; and a probe housing having a diaphragm, the proximal end of the shaft coupled to the diaphragm such that a long axis of the shaft orients substantially perpendicular to the diaphragm, the diaphragm providing axial displacement of the shaft relative to the probe housing.

28. The apparatus of claim 27 wherein the interstitial probe comprises a thermocouple coupled to the distal end of the shaft and in electrical communication with the control console.

29. The apparatus of claim 27 wherein the interstitial probe comprises a sheath having a sheath housing and a sheath tube coupled to the sheath housing, the sheath housing coupled to a probe housing associated with the proximal end of the shaft and the sheath tube extending about the shaft from the proximal end of the shaft to the distal end of the shaft, the sheath configured to insert within the infarcted zone of tissue.

30. The apparatus of claim 29 wherein a space between an inner wall of the sheath and the shaft defines a fluid communication pathway, the fluid communication pathway configured to allow fluid flow between a distal end of the interstitial probe and a proximal end of the interstitial probe.

31. The apparatus of claim 29 wherein the sheath comprises a fixation plug oriented at a proximal end of the sheath tube, the fixation plug configured to expand against a surgical opening formed within a tissue to seal the surgical opening.

32. The apparatus of claim 31 wherein the interstitial probe further comprises a fixating plug expansion tube oriented at the distal end of the shaft the fixating plug expansion tube configured to insert within the fixation plug of the sheath and expand the fixation plug against the surgical opening to seal the surgical opening.

33. The apparatus of claim 29 wherein the sheath housing comprises a pad having an antiseptic fluid, the pad oriented between the sheath housing and tissue of a surgical location.

34. The apparatus of claim 27 further comprising:
an umbilical coupled to the control console, in fluid communication with the control console and the cooling mechanism, in electrical communication with the control console, and in electrical communication with the coagulation mechanism, the umbilical having an umbilical retaining block; and
a shield coupled to a tissue of a surgical location and in communication with the umbilical retaining block of the umbilical.

35. A method for inducing hypothermia in a brain having an infarcted zone of tissue comprising:
surgically eating an opening within a skull of a head;
inserting a sheath having a sheath housing and a sheath tube coupled to the sheath housing into the brain;
placing a shaft of an interstitial probe within the sheath tube, the shaft having a proximal end and a distal end, the distal end of the shaft positioning within the infarcted zone of tissue of the brain, the distal and of the shaft having a cooling mechanism and the distal end of the shaft having a coagulation mechanism oriented at the distal end of the shaft;
cooling at least a portion of the infarcted zone of tissue of the brain with the cooling mechanism of the interstitial probe to induce hypothermia within at least a portion of the infarcted zone of tissue; and
coagulating at least a portion of the infarcted zone of tissue of the brain with the coagulation mechanism.

36. The method of claim 35 further comprising removing fluid from the at least a portion of the infarcted zone of tissue of the brain using a fluid communication pathway defined as a space between an inner wall of the sheath tube and the shaft of the interstitial probe.

37. The method of claim 35 further comprising delivering fluid into the at least a portion of the infarcted zone of tissue of the brain using a fluid communication pathway defined as a space between an inner wall of the sheath tube and the shaft of the interstitial probe.

38. An interstitial probe comprising:
a shaft having a proximal end and a distal end, the distal end of the shaft configured to position within an infarcted zone of tissue;
a cooling mechanism oriented at the distal end of the shaft, the cooling mechanism configured to induce hypothermia within at least a portion of the infarcted zone of tissue;
a coagulation mechanism oriented at the distal end of the shaft;
a sheath having a sheath housing and a sheath tube coupled to the sheath housing, the sheath housing coupled to a probe housing associated with the proximal end of the shaft and the sheath tube extending about the shaft from the proximal end of the shaft to the distal end of the shaft, the sheath configured to insert within the infarcted zone of tissue;
wherein the sheath housing comprises a pad having an antiseptic fluid, the pad oriented between the sheath housing and tissue of a surgical location.

39. An apparatus for inducing hypothermia comprising:
a control console; and
an interstitial probe coupled to the control console, the interstitial probe having:
a shaft having a proximal end and a distal end, the distal end of the shaft configured to position within an infarcted zone of tissue;
a cooling mechanism oriented at the distal end of the shaft, the cooling mechanism in fluid communication with the control console and configured to induce hypothermia within at least a portion of the infarcted zone of tissue;
a coagulation mechanism oriented at the distal end of the shaft, the coagulation mechanism in electrical communication with the control console; and
a sheath having a sheath housing and a sheath tube coupled to the sheath housing, the sheath housing coupled to a probe housing associated with the proximal end of the shaft and the sheath tube extending about the shaft from the proximal end of the shaft to the distal end of the shaft, the sheath configured to insert within the infarcted zone of tissue;
wherein the sheath housing comprises a pad having an antiseptic fluid, the pad oriented between the sheath housing and tissue of a surgical location.

* * * * *

UNITED STATES PATENT AND TRADEMARK OFFICE
CERTIFICATE OF CORRECTION

PATENT NO.         : 7,094,234 B1
APPLICATION NO. : 10/229218
DATED               : August 22, 2006
INVENTOR(S)       : Charles D. Lennox Page 1 of 1

It is certified that error appears in the above-identified patent and that said Letters Patent is hereby corrected as shown below:

At column 11, line 65, in claim 1, change "tire" to --time--.

At column 11, lines 66, in claim 1, change "an" to --than--.

At column 13, line 1, in claim 15, change "and" to --end--.

At column 13, line 59, in claim 18, change "my" to --may--.

At column 14, line 26, in claim 21, change "infracted" to --infarcted--.

At column 14, line 36, in claim 23, change "with" to --within--.

At column 15, line 20, in claim 29, change "infracted" to --infarcted--.

At column 15, line 53, in claim 35, change "eating" to --creating--.

At column 15, line 59, in claim 35, change "and" to --end--.

Signed and Sealed this

Nineteenth Day of December, 2006

JON W. DUDAS
*Director of the United States Patent and Trademark Office*